United States Patent [19]

Schooley et al.

[11] Patent Number: 5,082,828

[45] Date of Patent: Jan. 21, 1992

[54] ECLOSION HORMONE PEPTIDES

[75] Inventors: David A. Schooley, Reno, Nev.; Hiroshi Kataoka, Tokyo, Japan; Steven J. Kramer, Sunnyvale, Calif.

[73] Assignee: Sandoz Ltd., Basle, Switzerland

[21] Appl. No.: 645,088

[22] Filed: Jan. 22, 1991

Related U.S. Application Data

[63] Continuation-in-part of Ser. No. 451,289, Dec. 15, 1989, abandoned, which is a continuation-in-part of Ser. No. 223,139, Jul. 22, 1988, abandoned.

[51] Int. Cl.$^5$ .......................... A61K 37/02; C07K 7/10
[52] U.S. Cl. ........................................ 514/12; 530/324
[58] Field of Search ........................... 514/12; 530/324

[56] References Cited

PUBLICATIONS

Marti et al., "Microanalysis of the Amino Acid Sequence of the Eclosion Hormone from the Tobacco Hornworm Manduca Sexta" Febs Letters v219(2) pp. 415–418, Jul. 27, 1987.

Primary Examiner—Lester L. Lee

[57] ABSTRACT

Eclosion hormone (EH) was isolated and characterized using a variety of chromatographic techniques. EH is a polypeptide having 62 amino acids.

4 Claims, No Drawings

ECLOSION HORMONE PEPTIDES

This is a continuation-in-part of U.S. Pat. application Ser. No. 07/451,289, filed Dec. 15, 1989 and now abandoned, which is a continuation-in-part of application Ser. No. 07/223,139, filed July 22, 1988, and now abandoned.

This invention relates to the isolation and characterization of insect eclosion hormone (and derivatives thereof).

DESCRIPTION OF THE INVENTION

Eclosion hormone (EH) is a neuropeptide secreted by cells in the insect brain which initiates ecdysis (molting) behaviors as well as various other physiological responses. Synthetically produced or isolated forms of EH or its derivatives may be used as insecticides and insect population control agents as sufficient quantities of these hormones disrupt the normal growth and maturation processes.

Eclosion hormone was isolated from trimmed heads of pharate adult *Manduca sexta* by an eight step purification procedure: defatting, acid extraction of EH from tissue, ion exchange chromatography, reversed-phase cartridge chromatography, liquid chromatography (on two different semipreparative reversed-phase systems), ion exchange liquid chromatography, and analytical reversed-phase liquid chromatography. The product was a substantially homogenous polypeptide.

After purification, the complete amino acid sequence of EH was determined. The native EH peptide was found to involve a sequence of sixty-two (62) amino acids.

As used throughout the specification and claims, the following definitions will apply:

Eclosion hormone-like activity—activity of a polypeptide, observed in vivo or in vitro which mimics or is substantially the same as the activity of native eclosion hormone.

Native eclosion hormone (EH)—a polypeptide which is found naturally in certain insects which is involved in the behavioral events leading to initiation of ecdysis.

Associated insect polypeptides—polypeptides naturally found in an insect which are other than eclosion hormone.

DETAILED DESCRIPTION OF THE INVENTION

In accord with one aspect of the present invention, eclosion hormone has been purified and found to conform to the amino acid sequence of Formula I, presented below:

Asn Pro Ala Ile Ala Thr Gly Tyr Asp Pro Met
Glu Ile Cys Ile Glu Asn Cys Ala Gln Cys Lys
Lys Met Leu Gly Ala Trp Phe Glu Gly Pro Leu
Cys Ala Glu Ser Cys Ile Lys Phe Lys Gly Lys
Leu Ile Pro Glu Cys Glu Asp Phe Ala Ser Ile
    Ala Pro Phe Leu Asn Lys Leu    (Formula I)

wherein the C-terminus is in the free acid (Leu-OH) form.

Thus, this invention provides for polypeptides having eclosion hormone-like activity, which are substantially free from associated insect polypeptides and comprise or consist of the amino acid sequence of Formula I.

As seen in Formula 1, EH is a polypeptide having 62 amino acids. The peptide was digested using lysyl endopeptidase and then followed by reduction and carboxamidomethylation, yielding 3 fragments. These fragments were sequenced and the results are shown in Example 3, below. Cysteine residues were present in all fragment peptides as the modified form, carboxamidomethyl cysteine (indicated by Cys*) which allowed identification as the PTH-derivative.

Reduced carboxamidomethylated EH (RCAM-EH) was digested by endoproteinase Glu-C and yielded many fragments. Fragments G-1, G-2 and G-3 were sequenced and are given in Example 4.

To further characterize the carboxyl terminus, the free amino acids released during the lysyl endopeptidase digestion of intact EH were analyzed as phenylthiocarbamoyl (PTC)—amino acids. Besides PTC-Lys from the 23rd residue, only PTC-Leu-OH was found; no PTC-Leu-$NH_2$ was detected.

The polypeptide of this invention evokes a positive EH-like response when administered at a dose of 0.1 ng per pharate adult in the tobacco budworm *Heliothis virescens* and at 0.01 ng per second larval stadium of *M. sexta*.

This invention also provides for the use of EH and its derivatives for controlling the populations of insects, particularly against Lepidopteran larvae. One class of such insecticides, which is a contact insecticide, comprises an effective amount of EH or its derivatives combined with an inert carrier which does not adversely affect the active peptide ingredient, such as DMSO and water and various solid carriers such as inert clays, lactose, and proteinaceous materials such as defatted soybean powder. This composition is applied either directly to the insect or to its environment. The active ingredient disrupts the normal growth and maturation processes of the insects, resulting in insect death. Typical doses would range from 0.5–100 kg/hectare.

The following examples are offered by way of illustration, and are not intended to limit the invention.

EXAMPLE A

Bioassays

The biological activity of EH in fractions from each purification step is detected using a pharate adult *H. virescens* in vivo assay, similar to that described by Fugo (1983) *Appl. Ent. Zoo.* 18:540–44 and Truman (1973) *Biol. Bull.* 14:44:200–211, both of which are incorporated by reference. Insects are injected in the dorsal thorax with 5 μl aliquots dissolved in physiological saline, approximately 7 hr before normal eclosion, which occurs just after the onset of darkness. Moths eclosing within 3 hr of injection are scored as receiving EH, a positive response.

The biological activity of isolated EH is assayed as follows. Late second stadium *M. sexta* are selected for assay when third stadium mandibles are visible through the fluid-filled second stadium head capsule. Development of these larvae, held at 31° C., is checked at 15 min intervals until an air bubble first appears in the head capsule. "Air bubble" larvae are immediately injected in the dorsal abdomen with 1 μl of the test fractions, and time to molt of treated and controls is compared at room temperature ~21° C.). Mean time to molt for EH-affected larvae is 50 min; that for controls is 109 min. Purified EH is active at 0.1 ng per pharate adult *H. virescens*, and at 0.01 ng per second stadium *M. sexta*.

EXAMPLE B

As indicated by Copenhaver and Truman (1982), *J. Insect Physiol.* 28:695-701, EH can block the larval molt completely if it is present in the hemolymph during a particular sensitive period when it is normally absent. In this situation, treated larvae respond to EH with pre-ecdysis and ecdysis behavior, but are unable to shed the still attached epidermis. Once the ecdysis program has occurred, it is not repeated even if the insect's endogenous EH is present at the normal developmental stage.

An assay for detection and evaluation of insect control (insecticidal) activity of EH is based on contact and penetration of the hormones. DMSO is employed as a carrier to facilitate uptake. Accordingly, the EH to be evaluated is dissolved in about 30% aqueous DMSO and applied at several concentrations (1 mg/ml and 10-fold serial dilutions thereof) to a test group of age-synchronized lepidopteran insects (such as *Manduca sexta*) at the beginning of the first or second instar at 28° C. The prevention of normal molt of the treated group is compared to the normal ecdysis behavior of a control group receiving only DMSO solution.

EXAMPLE 1

Defatting, Extraction, and SP-Sephadex Chromatography

*M. sexta* are reared on an artificial diet as described by Bell et al. (1976) *Ann. Entomol. Soc. Am.* 69:365-373 and Troetschler et al. (1985) *J. Econ. Entomol.* 78:1521-1523, both of which are incorporated by reference. Pharate adult *M. sexta* are beheaded 24-48 hours before adult eclosion and the heads frozen. A posterior section of these heads containing the brain and the corpora cardiaca/corpora allata complex is punched out with a 5 mm diameter cork borer and stored at −80° C. until extraction.

Ten thousand trimmed *M. sexta* heads (wet weight ~420 g) are homogenized in 1500 ml cold (−20° C.) acetone with a Polytron homogenizer and filtered. Residues are extracted with 1500 ml 1M HOAc/20 mM HCl (containing 0.1 mM phenyl methylsulfonylfluoride and 0.01 mM Pepstatin A, freshly prepared) and centrifuged at 10,000×g for 20 min. After re-extraction of the pellet with 1200 ml of the same solution, and recentrifugation, the combined supernatants are applied directly to a SP-Sephadex C-25 column (25×750 mm, 300 ml bed volume) equilibrated with 1M HOAc. The column is eluted with 1000 ml each of 1M HOAc, 0.05M NH$_4$OAc (pH 4.0), and 0.05M, 0.1M, 0.4M, and 0.8M NH$_4$OAc (pH 7.0). EH is recovered in the 0.05M NH$_4$OAc (pH 7.0) fraction.

EXAMPLE 2

Further Purifications

Vydac C$_4$ cartridge: The SP-Sephadex fraction with EH activity from Example 2 is applied directly to 10 g of reversed-phase Vydac C$_4$ packing material (20-30 μm, contained in a 75 ml polypropylene syringe barrel) equilibrated with 0.1% trifluoroacetic acid (TFA). The cartridge is eluted with 100 ml each of 20%, 25%, 35%, 40%, and 50% CH$_3$CN in 0.1% TFA. EH was recovered in the 35% CH$_3$CN/0.1% TFA fraction.

Vydac C$_4$ semipreparative LC: For liquid chromatographic separations a Perkin-Elmer Model 410 Bio pumping system (titanium) with Model 7125 loop injection valve, and a Kratos Model 773 variable wavelength UV detector is used. The active fraction from the above step is diluted with 200 ml water and pumped onto a Vydac C$_4$ semipreparative column (10×250 mm) previously equilibrated with 15% 1-propanol (1-PrOH) containing 0.1% TFA. The sample is loaded through the pump by means of a Rheodyne Model 5302 valve mounted in the "D" solvent line. Retained materials are eluted via a 60 min linear gradient of 15-30% 1-PrOH in 0.1% TFA at a flow rate of 5 ml/min; 10 ml fractions are collected. EH active materials (which elute in the 20-26 min fractions) are combined and diluted with 60 ml water, and again pumped onto the same column, now equilibrated with 20% CH$_3$CN in 0.1% TFA. The column is eluted with an 80 min linear gradient of 20-40% CH$_3$CN in 0.1% TFA at a flow rate of 5 ml/min, with 10 ml fractions collected. EH is recovered in the 58-60 min fraction.

TSK DEAE-5PW LC: The active fraction from above is adjusted to pH 8.0 by addition of Tris, and applied to a TSK DEAE-5PW column (7.5×75 mm) equilibrated with 0.02M Tris-HCl buffer (pH 8.0) containing 10% CH$_3$CN. The column is eluted with two successive gradients at a flow rate of 1 ml/min; 60 min of 0-0.15M NaCl in 0.02M Tris-HCl buffer (pH 8.0) containing 10% CH$_3$CN, and 20 min of 0.15-0.5M NaCl in the same buffer. One ml fractions are collected. EH is recovered in the 42-45 min fractions.

Vydac C$_4$ analytical LC: Active fractions from above are combined and adjusted to pH 2.0 by addition of 1% TFA, and applied to a 5 μm Vydac C$_4$ column (4.6×150 mm) equilibrated with 30% CH$_3$CN in 0.1% heptafluorobutyric acid (HFBA). After elution with a 75 min gradient of 30-45% CH$_3$CN in 0.1% HFBA at a flow rate of 1.5 ml/min, pure EH is recovered in a peak at 32.8-34.2 min.

EXAMPLE 3

Lysyl Endopeptidase Digestion and Carboxamidomethylation

Purified EH from Example 2 (~400 pmol) is dissolved in 150 μl 3M urea, and 0.064 μg lysyl endopeptidase (Wako Chemical, Japan) in 50 μl 0.2M Tris-HCl (pH 9.0) is added to this solution. After incubation at 35° C. for 24 hr, 10 μg dithiothreitol in 200 μl M Tris-HCl (pH 8.5) containing 6M urea is added, and the mixture is incubated under argon at 45° C. for 1 hr. Next, 25 μg iodoacetamide in water is added, and the reaction mixture is maintained in the dark under argon at 21° C. for 20 min. After addition of formic acid to lower the pH, the reaction mixture is applied to a 5 μm Vydac C$_{18}$ column (4.6×100 mm). The fragment peptides are eluted with an 80 min gradient of 0-40% CH$_3$CN in 0.1% TFA at a flow rate of 0.5 ml/min.

The resulting 3 fragments are sequenced and the results are shown below. Cysteine residues are present in all fragment peptides as the modified form, carboxamidomethyl cysteine (indicated by Cys*) which allows identification as the PTH-derivative.

| Fragment | Amino Acid Numbers | Sequence |
| --- | --- | --- |
| L-1 | 1-22 | Asn Pro Ala Ile Ala Thr Gly Tyr Asp Pro Met Glu Ile Cys* Ile Glu Asn Cys* Ala Gln Cys* Lys |
| L-2 | 24-40 | Met Leu Gly Ala Trp Phe Glu Gly Pro Leu Cys* Ala Glu Ser Cys* Ile Lys |

| Fragment | Amino Acid Numbers | Sequence |
|---|---|---|
| L-3 | 45-61 | Leu Ile Pro Glu Cys* Glu Asp Phe Ala Ser Ile Ala Pro Phe Leu Asn Lys |

EXAMPLE 4

Endoproteinase Glu-C Digestion of Reduced Carboxamidomethylated EH (RCAM-EH)

Purified EH from Example 2 (650 pmol) is reduced and carboxamidomethylated by the same methods used for fragments from lysyl endopeptidase digestion in Example 3. The RCAM-EH is digested at 35° C. for 20 hr with 0.5 μg endoproteinase Glu-C (=protease V8, Boehringer Mannheim) in 500 μl 0.1M Tris-HCl (pH 8.0) containing 1M urea. After addition of 500 μl 1% TFA, the reaction mixture is applied to a 5 μm Vydac $C_{18}$ column (4.6×100 mm), and fragment peptides are eluted with an 80 min gradient of 0–40% $CH_3CN$ in 0.1% TFA at a flow rate of 0.3 ml/min.

The resulting fragments G-1, G-2, and G-3 are sequenced and are given below. However, as the fragments G-4 and G-5 coeluted, and the sequencing yield is low after Pro $_{57}$, the two sequences are considered tentative at this step.

| Fragment | Amino Acid Numbers | Sequence |
|---|---|---|
| G-1 | 1-12 | Asn Pro Ala Ile Ala Thr Gly Tyr Asp Pro Met Glu |
| G-2 | 17-36 | Asn Cys Ala Gln Cys* Lys Lys Met Leu Gly Ala Trp Phe Glu Gly Pro Leu Cys Ala Glu |
| G-3 | 37-48 | Ser Cys* Ile Lys Phe Lys Gly Lys Leu Ile Pro Glu |
| G-4 | 51-62 | Asp Phe Ala Ser Ile Ala Pro Phe Leu Asn Lys (Leu) |
| G-5 | 49-62 | Cys* Glu Asp Phe Ala Ser Ile Ala Pro Phe Leu Asn Lys (Leu) |

EXAMPLE 5

Proline-specific Endopeptidase Digestion of C-terminal Fragments

C-terminal fragments G-4 and G-5 obtained from endoproteinase Glu-C digestion of Example 4 are dissolved in 20 μl 0.05M phosphate buffer (pH 7.0) containing 0.1 μg proline-specific endopeptidase (Seikagaku Kogyo, Japan). After incubation at 35° C. for 1 hr, fragment peptides are separated with the same LC conditions as are used in Example 4. The peptides are sequenced and shown below.

These data allowed the unambiguous assignment of the three major fragments P-1, P-2 and P-3, which are given below. P-1 and P-3 contain proline at the carboxyl terminus where they were cleaved by the enzyme. Since P-2 contains leucine at the carboxyl terminus, it is concluded that leucine is the 62nd residue and the carboxyl terminus of intact eclosion hormone.

| Fragment | Amino Acid Numbers | Sequence |
|---|---|---|
| P-1 | 51-57 | Asp Phe Ala Ser Ile Ala Pro |
| P-2 | 58-62 | Phe Leu Asn Lys Leu |
| P-3 | 49-57 | Cys* Glu Asp Phe Ala Ser Ile Ala Pro |

EXAMPLE 6

Sequence Analysis

Purified EH and fragment peptides from enzymic digestion are sequenced using an Applied Biosystems Model 477A pulsed liquid phase protein sequencer. Released phenylthiohydantoin amino acids are analyzed using an on-line analyzer (Applied Biosystems, Model 120A).

EXAMPLE 7

Amino Acid Analysis

Purified EH and fragment peptides are hydrolyzed in vapor from 6M HCl/1% phenol (110° C. for 20 hr). Hydrolysates are analyzed after conversion to phenylthiocarbamoyl (PTC) amino acid derivatives by reversed-phase LC using an Ultrasphere ODS column (4.6×150 mm).

The starting buffer (D) is 0.05M sodium acetate containing 1.15 mM triethylamine and 2% methanol, adjusted to pH 6 with phosphoric acid. The eluting buffers are identical except for the organic solvent; B contains 50% methanol and C contains 50% $CH_3CN$. The column washing solvent (A) is 70% $CH_3CN$ in $H_2O$. Buffers are delivered by a Perkin-Elmer Series 4 pump using the following program. (Linear gradients were used between times indicated, except times marked with asterisk. These are step gradients or isocratic segments). The standard solvent program is modified by inserting an additional 30 min gradient segment from 49% to 100% buffer C at the end of the usual PTC-amino acid elution period to allow detection of PTC-Leu-$NH_2$ (e.g. 45 minutes).

| Time | Flow | A | B | C | D |
|---|---|---|---|---|---|
| 0 min | 1.0 ml/min | 0 | 0 | 0 | 100% |
| 21 min | " | 0 | 30% | 0 | 70% |
| 30 min | " | 0 | 0 | 35% | 65% |
| 45 min | " | 0 | 0 | 49% | 51% |
| 55 min | 1.5 ml/min | 100% | 0 | 0 | 0 |
| 71 min | 1.0 ml/min | 0 | 0 | 0 | 100% |
| 79 min* | " | 0 | 0 | 0 | 100% |

EXAMPLE 8

Characterization of Carboxyl Terminus

Purified EH (~400 pmol) is dissolved in 30 μl 0.02M $NH_4OAc$ (pH 8.5) containing 0.1 μg lysyl endopeptidase. After incubation at 35° C. for 2 hr, the reaction mixture is dried down and derivatized with phenyl isothiocyanate. The resultant PTC amino acids are identified using reversed-phase LC conditions modified to detect PTC-Leu-$NH_2$ by inserting an additional 30 min gradient segment from 49–100% buffer C of Ex. 7 after the end of the usual last linear gradient. The only PTC-amino acids detected are PTC-Lys (from Lys[23]) and PTC-Leu-OH. No PTC-Leu-$NH_2$ is found. Thus it is concluded that the carboxyl terminal residue is leucine in free acid form.

What is claimed is:

| Fragment | Amino Acid Numbers | Sequence |
|---|---|---|
| | | Ala Pro |

1. A polypeptide from *Manduca sexta* substantially free from associated insect polypeptides, having eclosion hormone-like activity.

2. A polypeptide free from associated insect polypeptides having an amino acid sequence conforming to the formula:

> Asn Pro Ala Ile Ala Thr Gly Tyr Asp Pro Met
> Glu Ile Cys Ile Glu Asn Cys Ala Gln Cys Lys
> Lys Met Leu Gly Ala Trp Phe Glu Gly Pro Leu
> Cys Ala Glu Ser Cys Ile Lys Phe Lys Gly Lys
> Leu Ile Pro Glu Cys Glu Asp Phe Ala Ser Ile
> Ala Pro Phe Leu Asn Lys Leu.

3. An insect-controlling composition comprising an insect population controlling effective amount of *Manduca sexta* eclosion hormone, substantially free from associated insect polypeptides and an inert carrier.

4. A method of controlling lepidopteran larvae comprising applying to such larvae or their environment an insect population controlling effective amount of the composition of claim 3.

* * * * *